(12) United States Patent
Teixeira et al.

(10) Patent No.: US 10,521,927 B2
(45) Date of Patent: Dec. 31, 2019

(54) INTERNAL BODY MARKER PREDICTION FROM SURFACE DATA IN MEDICAL IMAGING

(71) Applicant: Siemens Healthcare GmbH, Erlangen (DE)

(72) Inventors: Brian Teixeira, Verneuil-en-Halatte (FR); Vivek Kumar Singh, Princeton, NJ (US); Birgi Tamersoy, Erlangen (DE); Terrence Chen, Princeton, NJ (US); Kai Ma, Princeton, NJ (US); Andreas Krauss, Bubenreuth (DE); Andreas Wimmer, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/056,586

(22) Filed: Aug. 7, 2018

(65) Prior Publication Data
US 2019/0057515 A1    Feb. 21, 2019

Related U.S. Application Data

(60) Provisional application No. 62/545,562, filed on Aug. 15, 2017.

(51) Int. Cl.
*G06T 7/73* (2017.01)
*G06T 7/50* (2017.01)
*A61B 90/00* (2016.01)
*A61B 6/12* (2006.01)

(52) U.S. Cl.
CPC ............ *G06T 7/73* (2017.01); *A61B 6/12* (2013.01); *A61B 90/39* (2016.02); *G06T 7/50* (2017.01); *G06T 2207/10028* (2013.01); *G06T 2207/20076* (2013.01); *G06T 2207/20081* (2013.01);
(Continued)

(58) Field of Classification Search
CPC ... G06T 7/73; G06T 7/50; G06T 2207/10028; G06T 2207/20076; G06T 2207/20081; G06T 2207/20084; G06T 2207/30196; G06T 2207/30204; A61B 90/39; A61B 6/12
See application file for complete search history.

(56) References Cited

U.S. PATENT DOCUMENTS

| 6,125,345 A | * | 9/2000 | Modi ................ G10L 15/10 704/232 |
| 6,144,875 A | * | 11/2000 | Schweikard ......... A61N 5/1049 378/69 |
| 2016/0262714 A1 | | 9/2016 | Krauss et al. |

(Continued)

OTHER PUBLICATIONS

Yasrab et al. "An Encoder-Decoder Based Convolution Neural Network (CNN) for Future Advanced Driver Assistance System (ADAS)". Applied Science 2017, 7, 312 2017.*
(Continued)

*Primary Examiner* — Michael E Teitelbaum

(57) ABSTRACT

Machine learning is used to train a network to predict the location of an internal body marker from surface data. A depth image or other image of the surface of the patient is used to determine the locations of anatomical landmarks. The training may use a loss function that includes a term to limit failure to predict a landmark and/or off-centering of the landmark. The landmarks may then be used to configure medical scanning and/or for diagnosis.

12 Claims, 4 Drawing Sheets

(52) U.S. Cl.
CPC ............... *G06T 2207/20084* (2013.01); *G06T 2207/30196* (2013.01); *G06T 2207/30204* (2013.01)

(56) References Cited

U.S. PATENT DOCUMENTS

2016/0306924 A1* 10/2016 Singh ..................... G16H 30/00
2016/0321522 A1* 11/2016 Yuan .................... G06N 3/0454

OTHER PUBLICATIONS

U.S. Appl. No. 15/883,328, filed Jan. 30, 2018.
Long, Jonathan, Evan Shelhamer, and Trevor Darrell. "Fully convolutional networks for semantic segmentation." Proceedings of the IEEE conference on computer vision and pattern recognition., pp. 1-10, 2015.
Zeiler, Matthew D. "ADADELTA: an adaptive learning rate method." arXiv preprint arXiv:1212.5701, pp. 1-6, (2012).

* cited by examiner

INTERNAL BODY MARKER PREDICTION FROM SURFACE DATA IN MEDICAL IMAGING

RELATED APPLICATION

The present patent document claims the benefit of the filing date under 35 U.S.C. § 119(e) of Provisional U.S. Patent Application Ser. No. 62/545,562, filed Aug. 15, 2017, which is hereby incorporated by reference.

BACKGROUND

The present embodiments relate to predicting locations of internal markers for medical imaging. Internal anatomical structures may be used for medical scan planning, such as planning for computed tomography (CT), magnetic resonance (MR), fluoroscopy, or ultrasound scanning. For instance, for CT scanning, internal structures may be used to determine the scan range to obtain topogram or full CT scan, depending upon which organ needs to be scanned. For MR, the pulse sequence may be planned to reduce scan time by focusing on particular anatomy. For ultrasound, the internal region of interest for scanning may be more quickly located based on anatomical information.

The internal anatomical structures may be located by scanning a patient. Such scanning is time consuming and may subject the patient to ionizing radiation. There have been advances in realistic human body shape modeling and simulation in the graphics domain. Different statistical models have been applied to learn compact parametric representations of the human body shape. However, their impact on the healthcare domain is relatively limited. Existing shape modeling approaches focus primarily on the skin surface while the healthcare domain pays more attention to the internal organs.

SUMMARY

Systems, methods, and instructions on computer readable media are provided for internal body marker prediction from surface data in medical imaging. Machine learning is used to train a network to predict the location of an internal body marker from surface data. A depth image or other image of the surface of the patient is used to determine the locations of anatomical landmarks. The training may use a loss function that includes a term to limit failure to predict a landmark and/or off-centering of the landmark. The landmarks may then be used to configure medical scanning and/or for diagnosis.

In a first aspect, a method is provided for internal body marker prediction from surface data in a medical imaging system. A sensor captures an outer surface of a patient. The surface data is from the capturing of the outer surface of the patient. An image processor generates an image by a machine-learned network in response to input of the surface data to the machine-learned network. The image represents a location of the internal body marker of the patient. A display device displays the image.

In a second aspect, a method is provided for internal body marker prediction from surface data in a medical imaging system. A sensor captures an outer surface of a patient. The surface data is from the capturing of the outer surface of the patient. An image processor generates locations of a plurality of internal body markers of the patient by a machine-learned neural network in response to input of the surface data to the machine-learned neural network. A medical scanner is configured to scan the patient based on the internal body markers.

In a third aspect, a medical imaging system is provided for internal anatomy prediction. A depth sensor is configured to measure depths to a patient. An image processor is configured to apply a machine-learned neural network to depth information from the depths. The machine-learned neural network was trained to predict locations of landmarks for the internal anatomy from the depth information. A display is configured to display an image showing the predicted locations of the landmarks.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

The internal anatomy of a human body is estimated from the surface data. Internal body markers of the patient are predicted from the patient surface data. The surface measurements may be obtained using 2.5D depth sensors or by 3D reconstructions from multiple 2D images. The predicted internal anatomy includes positions of various internal body markers, such as lung center, lung top, kidney center, etc. Different body markers may be predicted for different purposes. The internal body marker positions are estimated from geometric measurements of the patient's body surface using deep machine learning algorithms. Machine learning learns a correlation between the surface data and the locations of internal anatomical structures without assuming to the correlation to be linear and thus providing more accurate, stable results. An augmented loss function coupled with deep learning enables learning a non-linear correlation model. This loss function may enable more stable training and provide more accurate results. The resulting trained model is more accurate than predicting the landmarks based on a mean statistical model.

In one embodiment, a 3D surface model of the patient is used to create a 2 channel 2D image representing the depth of the patient surface and the width of the patient at each pixel. Multiple internal body markers are regressed from the 2 channel 2D image. Regressing for a larger number of internal body markers appears to be better than regressing sparse body markers. Regressing additional markers serve as a regularization for other markers, which may be otherwise difficult to regress.

Figure 1:
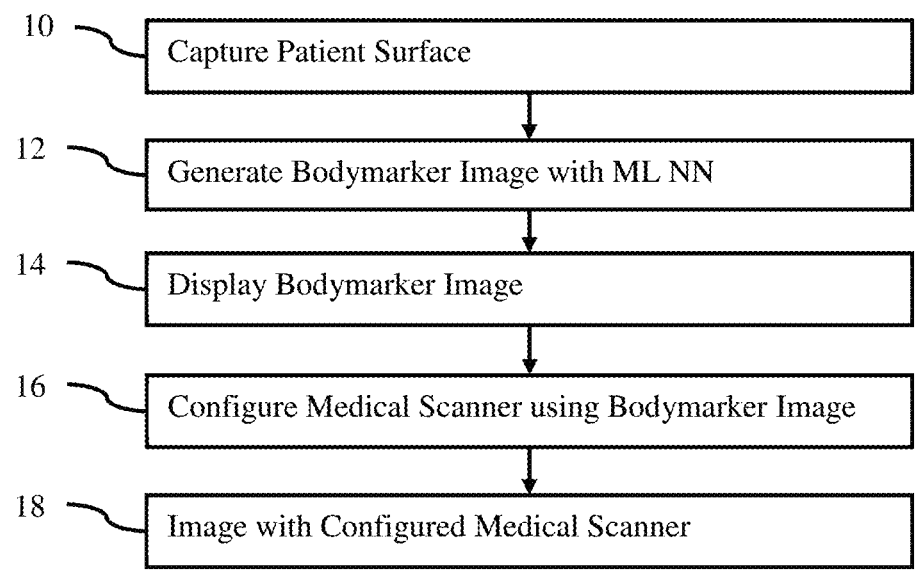
FIG. 1 is a flow chart diagram of one embodiment of a method for internal body marker prediction from surface data in a medical imaging system.

FIG. 1 is a flow chart diagram of one embodiment of a method for internal body marker prediction from surface data in a medical imaging system. A machine-learned network is used to generate an image of body markers (to generate the locations) from data representing an outside of the patient. The patient-specific point or region locations of one or more internal anatomical landmarks are determined by the network based on the surface data for the patient.

Rather than being a surface, the body markers are points or small volumes or areas representing a given anatomical landmark. A probabilistic distribution for a region may be used to indicate the location of a body marker (e.g., Gaussian distribution). The positions of any number of anatomical body markers may be predicted. For example, pubic symphysis, lung center, femur head right center, carina bifurcation, left common carotid artery, left hip bone, left kidney center, left kidney top, left lung top, liver bottom, liver center, liver top, right hip bone, right kidney center, right kidney top, right lung top, and sternum tip locations are predicted. Additional, different, or fewer anatomical body markers may be estimated. Different body markers may be estimated for different purposes, such as for different applications or type of scanning in a same imaging mode (e.g., CT) or for different types of imaging modes (e.g., CT vs. ultrasound vs. MR).

The method is performed in the order shown (e.g., top to bottom or numerical), but other orders may be used. Additional, different or fewer acts may be provided. For example, acts 16 and/or 18 are not provided. In another example, act 14 is not provided as the predicted marker distribution is used to configure for imaging without viewing by the operator.

In act 10, a sensor captures an outer surface of a patient. The sensor is a depth sensor, such as a 2.5D or RGBD sensor (e.g., Microsoft Kinect 2 or ASUS Xtion Pro). The depth sensor may be a camera or cameras capturing a grid projected onto the patient. The sensor may be multiple cameras capturing 2D images from different directions, allowing reconstruction of the outer surface from multiple images without transmission of structured light. Other optical or non-ionizing sensors may be used.

The sensor is directed at a patient. The sensor captures the outer surface of the patient from one or more perspectives. Any portion of the outer surface may be captured, such as the entire patient from head to toe and hand to hand on one side or just the torso. The sensor captures the outer surface with the patient in a particular position, such as capturing a front facing surface as the patient lies in a bed or on a table.

The outer surface is the skin of the patient. In other embodiments, the outer surface includes clothing. The sensor may use a frequency that passes through clothing and detects skin surface.

The outer surface is captured as depths from the sensor to different locations on the patient, an image or photograph of the outside of the patient, or both. The sensor outputs the sensed image and/or depths. Alternatively, the sensor measurements are processed to determine the outer surface information, such as stereoscopically determining the outer surface from camera images from different angles with image processing.

The measurements of the outer surface from the sensor are surface data for the patient. In one embodiment, the measurements or other output of the sensor are used to determine the surface data. The output is processed to determine the surface data. For example, a statistical shape model is fit to the depths. The statistical shape model is a mesh or other representation of an average or other statistical representation of an outside of a human or part of a human. The statistical shape model includes probabilities or other constraints on alteration, so that the fitting maintains the shape based on statistics. The surface data is then determined from the fit statistical shape model, such as depths from a point to the model.

Figure 2:
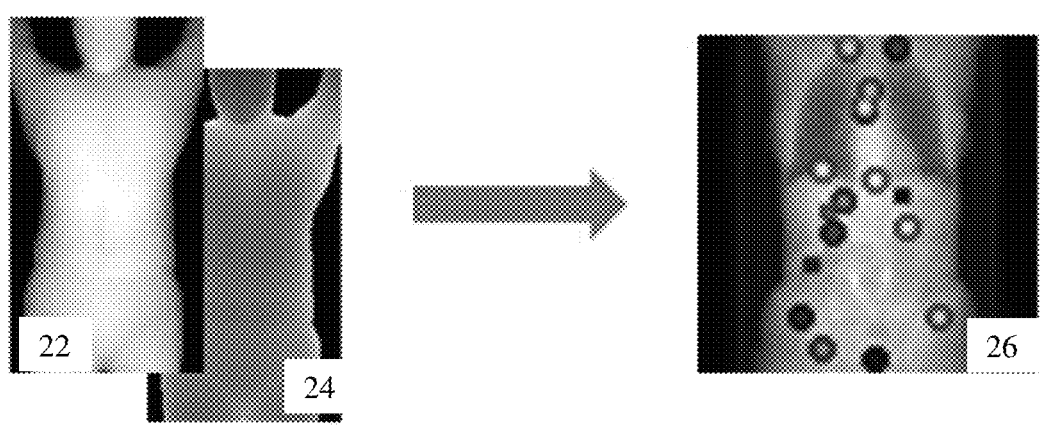
FIG. 2 illustrates example 2-channel surface data for predication of body marker locations.

In one embodiment, a 3D surface is used as the surface data without fitting the shape model, and/or the 3D surface from the fit shape model is used as the surface data. The surface data may include different representations of the patient. Two or more channels are created. FIG. 2 shows an example where the images 22, 24 have pixel intensity modulated by the amplitude of the channel. Given a 3D surface of the patient's body (skin surface), 2D projections of this data—skin surface image (e.g., height of the surface from the scanner table at each location in the image) and depth image (e.g., measure the thickness of the person at each location in the image)—are formed by image processing. Each channel provides different information. One channel provides a distance or height of front surface locations to a bed or table on which the patient lies, to the sensor, and/or relative to another location. The outer surface as sensed and the known location of the sensor to the bed are used to determine the distance. Another channel is a thickness of the patient. The thickness may be a difference of a given depth from the maximum and minimum depth for the fit model. Other thickness may be used. The 3D human surface mesh data is represented with a 2-channel 2D image—the first channel stores the depth of the body surface as observed from front, and second channel stores the thickness computed by measuring the distance between the closest and furthest point as observed from the front. Other channels may be used, such as one channel for depth from the sensor and another channel for optical image of the patient. Other surface data may be used.

The surface data is used at the resolution of the sensor. For example, the surface data is at 256×256 pixels. Other sizes may be used, including rectangular fields of view. The surface data may be filtered and/or processed. For example, the surface data is altered to a given resolution. As another example, the surface data is down sampled, such as reducing 256×256 to 64×64 pixels. Each pixel may represent any area, such as each pixel as down sampled to 64×64 representing 1 $cm^2$ or greater. Alternatively, the sensor captures at this lower resolution. The surface data may be cropped, such as limiting the field of view. Both cropping and down sampling may be used together, such as to create 64×64 channel data from 256×312 or other input channel data. Greater or lower resolution may assist in regression.

In another approach, the surface data is normalized prior to input. A plurality (e.g., 3 of the 17) of the internal body markers to be predicted or other markers (e.g., external skin locations) are located for normalization. Any detection may be used, such as detecting with one or more machine-learned networks. For example, landmark-specific networks are separately trained to detect the 3 or other number of landmarks from the surface data.

The machine-learned network for normalization is different than the network used for predicting all the body markers. Alternatively, the network for predicting is applied multiple times where the first or earlier time is used to locate some but less than all body markers for normalization.

Once a particular subset of body markers is located, the surface data is rescaled, resized, warped, or shifted (e.g., interpolation) so that the same landmarks are at the same locations in each sample or set of the surface data, normalizing the surface data. For example, the top of the surface data image is defined by the mean between left lung top and right lung top, and the bottom is defined by the pubic symphysis. The normalized surface data is then input for determination of other body markers or all the body markers including the ones previously predicted for normalization.

The locations of internal body markers are predicted from the surface data. The image 26 shows a distribution of 17 different body markers predicted from the two-channel input images 22, 24. The locations may be part of an image or may be a distribution in space separate from the image (e.g., graphical overlays that may be displayed over the image or without the image). In FIG. 2, the body markers are part of a topogram or x-ray projection predicted from the input surface data 22, 24. Other images may be used, such as the surface data as captured by the sensor and/or the surface data as one of the channels.

The locations are in two dimensions but may be locations in three dimensions. The internal body markers and locations may be predicted from only the surface data or may be predicted from the surface data and other data, such as patient height, weight, or body mass index.

In act 12, an image processor generates the image with the body markers and/or prediction of body marker locations. The surface data with or without other data are input to a machine-learned network and scalar or display values for the predicated locations are output. For example, a depth and thickness surface data images 22, 24 of the outer surface are input as two channels to the machine-learned network, which outputs a distribution of landmarks. The landmarks may or may not be labeled. FIG. 2 shows an example where a surface depth image 22 and a surface thickness image 24 are input to output an image of the landmark locations 26. The image processor applies the machine-learned network for body marker prediction. Any inputs for which the network is trained to use are applied as an input feature vector, such as just the surface data. The outputs are points for locations. Alternatively, a Gaussian or other distribution representing a probability of location for each landmark is output, such as outputting a heat map.

The machine-learned network is an image-to-image network trained to convert surface data to an image of locations of body markers. For example, the trained convolution units, weights, links, and/or other characteristics of the network are applied to the surface data and/or derived feature values to extract the corresponding features through a plurality of layers and output the body markers. The features of the input images (e.g., surface data) are extracted from the images. Other more abstract features may be extracted from those extracted features using the architecture. Depending on the number and/or arrangement of units or layers, other features are extracted from the input.

For training the machine-learned network, the machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

Figure 3:
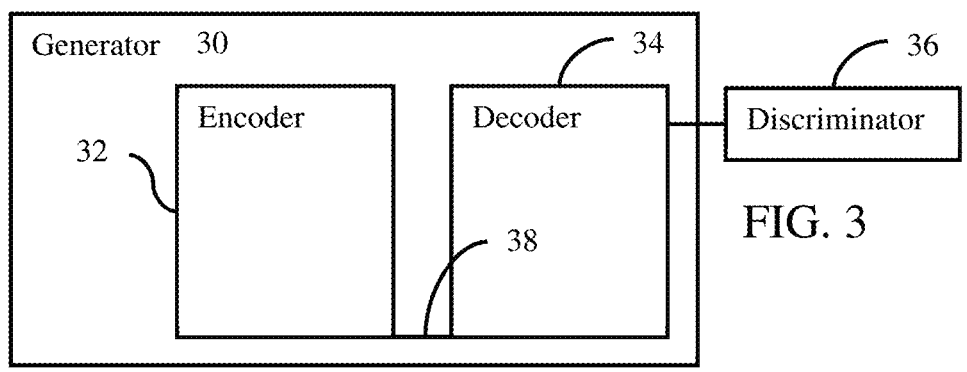
FIG. 3 is a block diagram of one embodiment of a network.

The machine learning network is an image-to-image network. Any machine training architecture for outputting a spatial distribution from an input spatial distribution may be used, such as a neural network. For example, U-Net or other fully convolutional network is used. A convolutional-to-transposed-convolutional network is used. One segment of layers or units applies convolution to increase abstractness or compression. The most abstract feature values are then output to another segment at a skip or bottleneck connection. The other segment of layers or units then applies transposed-convolution to decrease abstractness or compression, resulting in outputting the body markers or indication of class membership by location. FIG. 3 shows an example fully convolutional network as a GAN, but non-GAN (i.e., without a discriminator 36) may be used. The GAN includes a generator 30, such as U-Net, and a discriminator 36. The generator 30 includes an encoder (convolutional) network 32 and decoder (transposed-convolutional) network 34 forming a "U" shape with a connection between passing features at a greatest level of compression or abstractness from the encoder 32 to the decoder 34. A bottleneck connection 38 passes features from the encoder 32 to the decoder 38. Additional skip connections between the encoder 32 and decoder 34 at other scales may be used. Any now known or later developed U-Net or image-to-image architectures may be used. Other fully convolutional networks may be used.

For applications, the generators 30 of the GANs are used without the discriminator 36. The GANs are applied to the patient surface data by the generator 30 without the discriminator 36. The discriminator 36 is used for training.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Figure 4:
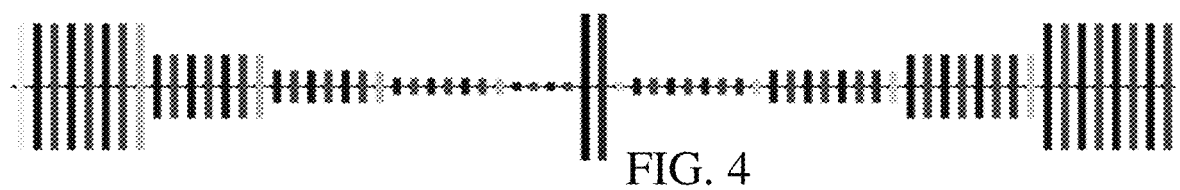
FIG. 4 shows an example fully convolutional network for predicting body markers from surface data.

FIG. 4 shows one embodiment of an image-to-image network. The encoder includes layers 5 scales (represented by vertical extent of the layers), and the decoder includes layers at 4 scales. The layers may be input, dropout, pooling, max-pooling, reshaping, activation, spatial dropout, batch normalization, dense, convolutional, up sampling, and/or other types of layers.

Figure 6:
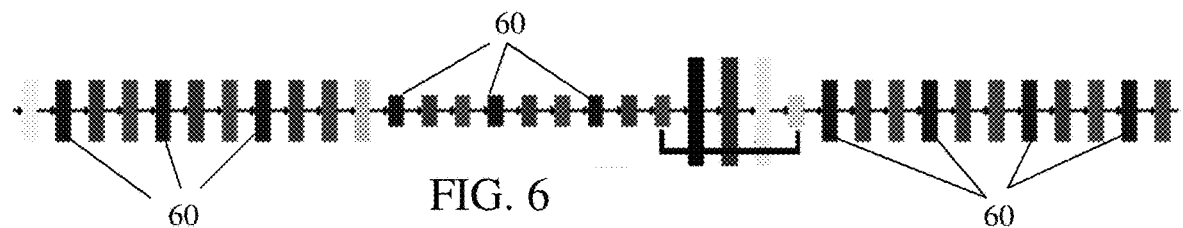
FIG. 6 shows another example fully convolutional network for predicting body markers from surface data.

FIG. 6 shows another embodiment of an image-to-image network. The encoder includes 2 scales and the decoder has one scale after an up-sampling layer up samples an output of the bottleneck connection passing features from the encoder to the decoder. A fully connected layer (e.g., dense layer) may be at the bottleneck of the network (i.e., between the encoder 32 and decoder 34 at a most abstract level of layers).

The fully connected layer may make sure as much information as possible is encoded. Batch normalization may be added to stabilize the training.

In the neural network of FIG. 6, the bottleneck connection includes a dense layer, followed by a spatial dropout layer, and then a reshaping layer prior to an up-sampling layer. The encoder includes 6 convolutional layers 60, and the decoder includes 4 convolutional layers 60. The same number of scales and/or convolutional layers 60 may be provided in the encoder and decoder. The layers at the greatest scale of the encoder include, in order, an input, convolutional, batch normalization, activation, convolutional, batch normalization, activation, convolutional, batch normalization, activation, and then max pooling to reduce the scale. The layers at the lowest scale of the encoder include, in order, convolutional, batch normalization, activation, convolutional, batch normalization, activation, convolutional, batch normalization, activation, and activation. After up sampling, the layers of the decoder include, in order, convolutional, batch normalization, activation, convolutional, batch normalization, activation, convolutional, batch normalization, activation, convolutional, and activation. Additional, different or fewer layers may be provided at any scale or as part of the skip connection. Additional scales may be provided.

Rather than pre-programming the features and trying to relate the features to attributes, the deep architecture (i.e. neural network) is defined to learn the features at different levels of abstraction based on an input image with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction.

In one embodiment, the body marker prediction is treated as an image-to-image translation problem. Starting from 2 channel images (e.g., distance and thickness for the outer surface), a single channel image (e.g., body marker distribution) of the same size is regressed. The output may be an image of i channels where i is the number of landmarks. This approach provides a neural network able to capture the features in the input image to retrieve the output image, which consists, in a sense, of a more 'complete' version of the input. In this fully convolutional network (FCN), the encoder 32 'encodes' the useful features of the input needed to regress the target, while the decoder 34 tries to use these features to create the targeted image.

A GAN or a generator 30 trained without a discriminator 36 may be used. GANs generate realistic images in image-to-image translation problems. GANs train two different networks simultaneously, the discriminator 36 whose purpose is to decide whether a given image is real or fake, and the generator 30 whose purpose is to fool the discriminator 36 by making images as realistic as possible.

For training any of the networks, any number of samples in the training data may be used. For example, 1000 training examples with 100 for testing and 100 for validation are used. Various optimizers may be used, such as Adadelta, SGD, RMSprop, or Adam. The weights of the network are randomly initialized, but another initialization may be used. End-to-end training is performed, but one or more features may be set. Batch normalization, dropout, and data augmentation may be used. During the optimization, the different distinguishing features are learned. The features providing an indication of landmark location given input surface data are learned.

The optimizer minimizes an error or loss, such as the Mean Squared Error (MSE), Huber loss, L1 loss, or L2 loss. Other losses may be used. In one embodiment, a joint loss function is used. The joint loss function is a combination of MSE, Huber, L1, or L2 with a further augmentation—a penalty. The penalty accounts for difficulties in the primary loss or error in dealing with landmark prediction from surface data, such as being a penalty for off-center shifting and/or missing landmarks.

Figure 5:
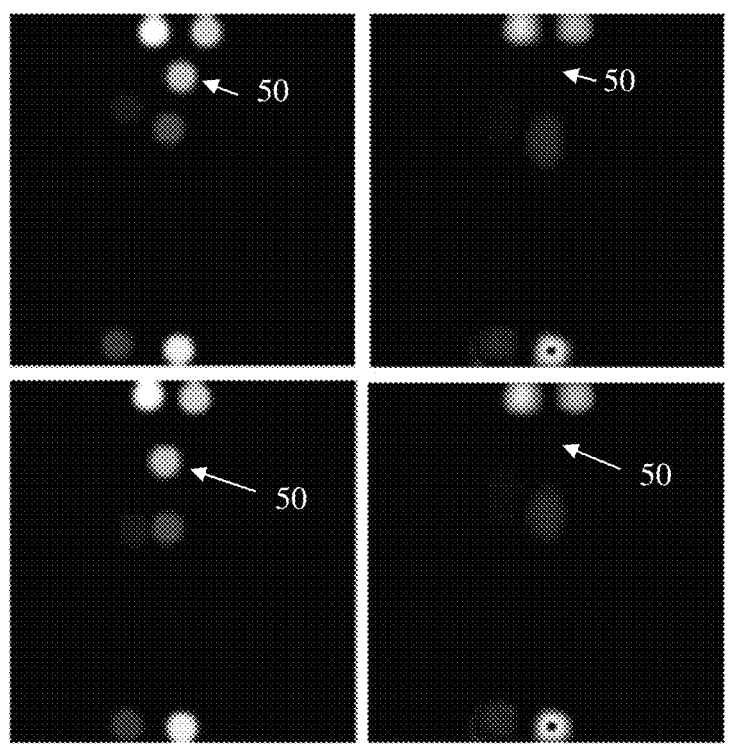
FIG. 5 shows two ground truth images of body marker locations and two generated images of body marker locations using the fully convolutional network of FIG. 4.

For example, FIG. 5 shows two examples of ground truth landmark locations (left side top and bottom) and predicted locations (right side top and bottom) using the neural network of FIG. 4 with a fully connected layer at the bottleneck (i.e., bottleneck connection 38). Using Adadelta optimizer with MSE as the objective function, 17 landmarks are predicted based on 256×256 normalized training surface data of 1000 samples. FIG. 5 shows extraction of 6 of the landmarks. The predicted landmarks are close to the mean, responding poorly to patient specific variation. MSE may lead to some of the landmarks being off-centered. Some landmarks 50 are missing. According to the loss (MSE), it is better to regress nothing than regressing a landmark at a wrong position. As MSE is comparing values pixel per pixel, when a landmark is regressed at a wrong position, the landmark is penalized twice: once where the landmark should be, and once where the landmark actually is. Therefore, if a bad initialization places a landmark at a wrong position, MSE may prefer predicting no landmarks after a few iterations. Moreover, L2 loss tends to regress blurred results.

The joint loss function with the added penalty term is used for some embodiments to address one or more of these issues. The joint loss function, using the penalty term, may be designed to overcome or reduce poor performance using a standard loss (e.g., MSE) or any other loss. For example, the penalty term penalizes the landmarks when the center of the landmark (e.g., Gaussian) is not where it should be, penalizes missing landmarks, and/or makes sure the overall image looks like a heat map of Gaussian distributions for the landmarks.

In one embodiment, the joint loss includes MSE, but other standard losses (e.g., L1, or Huber) may be used. For example, the joint loss is given by:

$$\frac{1}{B_s}\sum_{i=0}^{B_s}(Y_i - \hat{Y}_i)^2 + \delta_i$$

where i is an index for the landmarks, $B_s$ is the batch size, $Y_i$ is the output channel representing the ith landmark, and $\delta_i$ defines the custom loss or penalty term. The penalty term is added to the summation of MSE. Other functions may be used, such as including the penalty term as a weight, ratio, multiplication, subtraction, division, and/or other factor (e.g., in an exponential).

The penalty term, in one example, is given by:

$$\delta_i = \gamma \sum_{j=0}^{N} \alpha_j \left( \sqrt{(\text{argmax}(Y_i^j) - \text{argmax}(\hat{Y}_i^j))^2} + |\max(Y_i^j) - \max(\hat{Y}_i^j)| \right)$$

where N is the number of landmarks being regressed, $\gamma$ is a loss regularizer to make sure both MSE and custom loss are in the same order, $\alpha_j$ is a coefficient for the $j^{th}$ landmark, depending on how hard the landmark is to regress where $\Sigma\alpha_j=1$ so that landmarks more easily regressed are more influential in the regression of other landmarks, and $Y^j$ is the channel representing the $j^{th}$ landmark for the $i^{th}$ example. The Hat symbol is used to designate the ground truth (real) position. The difference between y and y hat compares the prediction of the network with the ground truth. The square root portion penalizes landmarks being off-center, and the absolute value portion penalizes missing landmarks. Both terms allow for precision in heat map distribution. Other functions may be used. The penalty term may include terms for dealing with any of various problems other than, in addition to, or without the off-centering or missing landmark terms. The penalty may be characterized as a reward.

Figure 7:
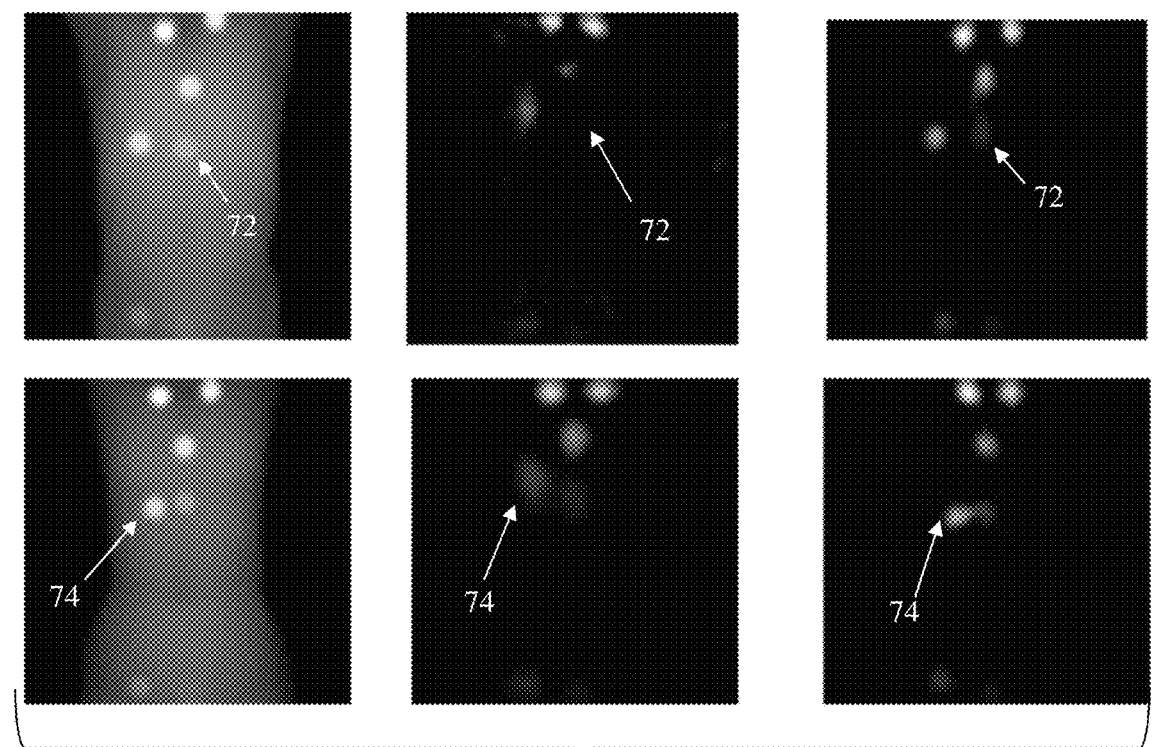
FIG. 7 shows two example ground truth images of body marker locations, two generated images of body marker locations using MSE loss function, and two generated images of body marker locations using a joint loss function.

With this joint loss, landmarks are less likely to be missing, the landmarks are more likely to be centered, and results are more likely to be different from one patient to another. FIG. 7 shows an example where the neural network of FIG. 6 is trained. The surface data is down sampled prior to input to 64×64. The convolution filter size for FIG. 5 is 5×5 and is increased to 11×11 for FIG. 7. Other sizes may be used. The left images (top and bottom) show two example ground truth landmark distributions. The center images (top and bottom) show use of MSE loss where the landmark 72 is missing and the landmark 74 is off-center and blurred. The right images (top and bottom) show predicted landmarks using the joint loss. The landmark 72 is provided and the landmark 74 is centered better and less blurry. In general, the joint loss results in more precise landmark distribution. Using just MSE but with reduced input resolution and larger convolution filter addresses some issues in prediction, such getting different results for different patients (i.e., predicting away from the mean at times). Using the joint loss function provides for even more accurate patient-specific prediction but with fewer missing landmarks and better centering.

In another embodiment, the joint loss function is used with pre-training and/or in an iterative approach. Even though this joint loss results in better prediction, pretraining with MSE or other standard loss may further improve prediction. The joint loss is used to fine tune the machine-learned network. The network based on the MSE loss is used as an initialization. The joint loss is then applied with the same or different training data to refine the network. Further refinement may be provided by using MSE or other standard loss again with the network based on the tuning or further training with the joint loss. This model is thus trained once with MSE, then with joint loss, and then with MSE. Other combinations may be used, such as using different standard error, ending with joint loss, starting with joint loss, and/or including other fine-tuning losses.

An iterative approach may be used. MSE is applied initially, then the joint loss, then the training is repeated any number of times cycling between MSE and joint loss. MSE and joint loss are sequentially used to re-train. The initial and final training may use MSE but joint loss for both initial and final or joint for one and MSE for another may be used in other approaches. Other standard losses may be used. Additional or different losses may be used, such as iterating training through three different losses including joint loss in any pattern.

Any number of iterations may be used, such as 100. The joint loss is good for fine tuning but may benefit from L2 regularization. The iterations continue until the MSE (i.e., L2) is not decreasing over a given number of iterations. Once the standard loss is not decreasing, the training ends.

The error of the loss is measured along the x and y axes. In other embodiments, the error is along just the y axis (i.e., long axis of the patient). The error is for one, a subset, or all landmarks. For example, the mean error for the different landmarks in the y-axis is used.

The machine-learned network is trained to predict point locations or a heat map (e.g., Gaussian distributions) for any number of body markers, such as 17. The output is an image showing the combination of locations for the different body markers. Alternatively, separate channels are output, such as separately outputting the locations or distributions for each of the body markers. For example, a 17-channel image is output where each channel describes a specific landmark, represented by a Gaussian heat map. Each channel is annotated or labeled with the name of the landmark.

Once trained, the model may be applied to estimate locations of body markers from input surface data. The many samples in the training data (e.g., surface data and ground truth locations of body markers) are used to learn to output the body markers. The machine learning model is trained to learn the correspondence between the surface data and the body markers.

The output of the trained network is an image representing a location of the internal body marker of the patient. More than one internal body marker may be represented in the same image, such as representing a distribution of labeled body markers. Any number of body markers may be used, such as 17. Some landmarks are more difficult to regress than other ones. Some landmarks may be correlated, meaning that some 'easy' landmarks may help regressing 'harder' landmarks. By training for a plurality of landmarks (e.g., 17 instead of 7), the mean error (e.g., 2D error) may be reduced. For example, using the 17 landmarks listed above instead of just the sternum tip, left lung top, pubic symphysis, liver top, lung center, femur head right center, and right lung top may reduce the mean error by 10% while deducing 10 additional useful landmarks.

In act 14 of FIG. 1, a display device displays the body marker locations. The display is a visual output. The image processor generates an image. A body marker image is generated and displayed on the display screen. The image may be output to a display, into a patient medical record (memory), and/or to a report.

The image is generated as a graphic showing locations. Alternatively, the image is generated as a medical image representing the outer surface (e.g., a camera image) or the internal tissue (e.g., predicted topogram or actual topogram) with the landmarks highlighted. Graphics may be added, overlaid, or embedded in the medical image. The image may be the landmark distribution without representing other anatomy.

The body markers may be labeled in the image. Annotation may provide alphanumeric text with the name of a given body marker. Color and/or symbol shape or size may be used to indicate different landmarks. Labeling is not provided in other embodiments.

The table below shows a comparison between the various approaches to predict the 17 landmarks through regression. The errors are in cm. The baseline is an error of the center locations of the landmarks as a mean from the patient-specific ground truth. The iterative approach uses the joint loss and MSE in iteration until the MSE does not decrease between iterations.

| | Mean 2D error | Mean Y error | 95% Y error |
|---|---|---|---|
| Baseline (Mean) | 2.60 | 2.09 | 5.33 |
| MSE | 2.44 | 2.03 | 4.67 |
| Iterative | 2.04 | 1.64 | 4.52 |

The iterative loss approach performs with the least error. The MSE approach is better than using the baseline.

The image may be used for diagnosis or other purpose by the user. For example, the image is used to position a patient, such as moving the patient along a longitudinal axis so that a given landmark or organ is centered with respect to a medical scanner. The image may be used to determine relative position of landmarks for diagnosis.

In act 16, the image processor configures the medical scanner based on the body markers. The medical scanner may configure itself. The image processor may provide information to a controller of the medical scanner to configure. The image processor may configure by direct control the medical scanner. Alternatively, the user manually configures the medical scanner based on the predicated landmarks by entry with one or more controls.

The prediction of certain internal anatomical body markers may assist in planning a medical scan. The body marker locations may be used to plan for scanning by any modality, such as CT, MR, fluoroscopy or ultrasound. For CT scanning, the body markers may be used to determine the scan range, depending upon which organ needs to be scanned and how accurately the nearby structures may be predicted. This may reduce the amount of ionizing radiation applied to the patient. The location of internal anatomical structures reflected by the body markers may assist in coil placement for MR scanning. For ultrasound scanning, the body markers may assist in probe guidance by providing approximate position. For fluoroscopy using dyna-CT scans, the body markers may be useful for positioning the patient and/or the scanner. Any setting or parameter of the medical scanner may be determined or configured based on the predicated body markers.

The predicted body markers may be used for anatomical anomaly detection. The predicted body markers are a representation of healthy anatomy learned from healthy patients. Body markers detected from a real or actual X-ray image of the patient may be compared with the predicted body markers. By quantifying the difference in location, any anatomical anomalies may be detected.

In act 18, the configured medical scanner scans the patient. The patient is imaged. The imaging is performed based on the configuration of the medical scanner. The scan range, focus, field of view, and/or other imaging parameters are based on the location or locations of one or more of the predicted body markers. The resulting image from the scanning more likely shows the region of interest. Ionizing radiation from the scanning may be limited based on the configuration using the predicted body markers.

Figure 8:
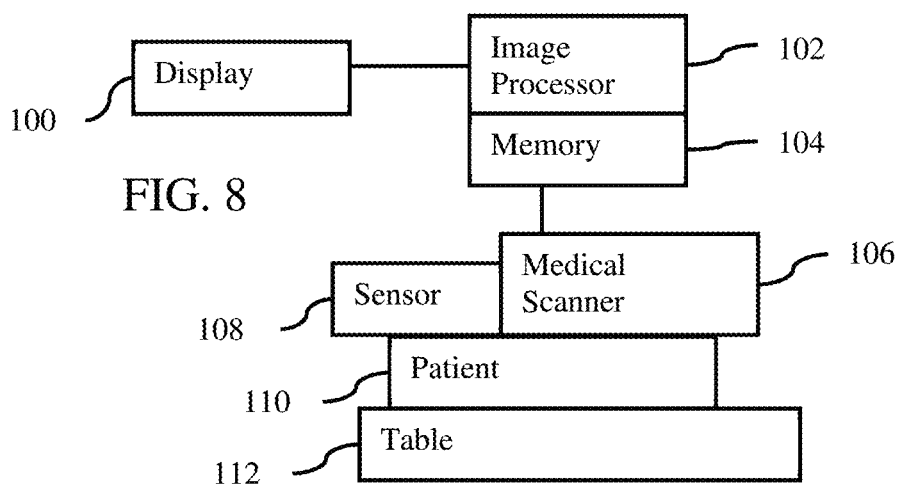
FIG. 8 is a block diagram of one embodiment of a system for internal anatomy prediction.

FIG. 8 shows one embodiment of a medical imaging system for internal anatomy prediction. The medical imaging system includes the display 100, memory 104, and image processor 102. The display 100, image processor 102, and memory 104 may be part of the medical scanner 106, a computer, server, workstation, or other system for image processing medical images from a scan of a patient. A workstation or computer without the medical scanner 106 may be used as the medical imaging system. The medical imaging system also includes the sensor 108 for sensing an outer surface of a patient.

Additional, different, or fewer components may be provided. For example, a computer network is included for remote image generation of locally captured surface data or for local image generation from remotely captured surface data. The machine-learned network is applied as a stand-alone application on the workstation or a local device or as a service deployed on network (cloud) architecture. As another example, a user input device (e.g., keyboard, buttons, sliders, dials, trackball, mouse, or other device) is provided for user alteration or placement of one or more markers (e.g., landmarks).

The sensor 108 is a depth sensor. LIDAR, 2.5D, RGBD, stereoscopic optical sensor, or other depth sensor may be used. One sensor 108 is shown, but multiple sensors may be used. A light projector may be provided. The sensor 108 may directly measure depth. The sensor 108 may include a separate processor for determining depth measurements from images, or the image processor 102 determines the depth measurements from images captured by the sensor 108. The depth may be relative to the sensor 108 and/or a bed or table 112.

The sensor 108 is directed to the patient 110. The sensor 108 may be part of or connected to the medical scanner 106 or is separate from the medical scanner 106.

The sensor 108 is configured to measure depths to or for a patient. The depths are distances from the sensor 108, table 112, or other location to the patient at various locations on the patient. Any sample pattern over the patient may be used. The sensor 108 outputs depth measurements and/or a surface image. The image processor 102 or another processor may fit a model to the sensor output to provide surface data. Alternatively, the sensor 108 outputs the surface data as the measurements.

The image processor 102 is a control processor, general processor, digital signal processor, three-dimensional data processor, graphics processing unit, application specific integrated circuit, field programmable gate array, digital circuit, analog circuit, combinations thereof, or other now known or later developed device for processing surface data. The image processor 102 is a single device, a plurality of devices, or a network. For more than one device, parallel or sequential division of processing may be used. Different devices making up the image processor 102 may perform different functions, such as applying the machine-learned network and configuring the medical scanner 106. In one embodiment, the image processor 102 is a control processor or other processor of a medical diagnostic imaging system, such as the medical scanner 106. The image processor 102 operates pursuant to and is configured by stored instructions, hardware, and/or firmware to perform various acts described herein.

The image processor 102 is configured to train a machine learning architecture. Based on a user provided or other source of the network architecture and training data, the image processor 102 learns features for encoders, decoders, discriminators, or other network parts to train the neural network. The result of the training is a machine-learned network or networks for body marker prediction.

Alternatively or additionally, the image processor 102 is configured to apply one or more machine-learned networks. For example, an image-to-image or other neural network is applied to surface data from the sensor 108. The machine-learned neural network is applied to surface information. Based on the previous training, the network predicts the locations of landmarks in response to application of the surface data (e.g., depth information from measured depths). The network may receive depth information for the outside of the patient as inputs. The neural network may output a landmark probability map (e.g., heatmap).

The machine-learned neural network predicts the landmarks based on having been trained with a joint loss function. The use of the joint loss function in training results of more accurate prediction of the landmarks in application. The joint loss function includes a standard or other error term and a penalty term. The penalty term includes functions for penalizing or rewarding based on centering, missing landmarks, size of distribution, and/or other landmark prediction characteristics. In one embodiment, the joint loss is used for sequential iteration using the error term and the joint loss in training.

The image processor 102 is configured to generate an image. The landmarks output from the neural network may be an image, spatial distribution of landmarks, and/or heat map. Annotations or graphics, such as for the landmarks, may be added to the image.

The display 100 is a CRT, LCD, projector, plasma, printer, tablet, smart phone or other now known or later developed display device for displaying the output, such as an image of the landmarks. The display 100 displays a medical image of locations of landmarks generated from the depth information.

The sensor measurements, fit shape model, surface data, network definition, features, machine-learned network, landmark images, output landmark locations, and/or other information are stored in a non-transitory computer readable memory, such as the memory 104. The memory 104 is an external storage device, RAM, ROM, database, and/or a local memory (e.g., solid state drive or hard drive). The same or different non-transitory computer readable media may be used for the instructions and other data. The memory 104 may be implemented using a database management system (DBMS) and residing on a memory, such as a hard disk, RAM, or removable media. Alternatively, the memory 104 is internal to the processor 102 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 104). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The medical scanner 106 is a medical diagnostic imaging system configured to scan an internal region of a patient and generate anatomical information from the scan. The medical scanner 106 is a CT, MR, PET, SPECT, X-ray, or ultrasound scanner.

The medical scanner 106 is configured to generate anatomical information. The configuration uses settings for one or more parameters, such as an X-ray source voltage, table position and/or range of movement, gantry position and/or range of movement, focus, field of view, scan density, detector thresholds, transmission sequence, image processing settings, filtering settings, or image generation settings. Based on landmarks generated from the surface data rather than scanning by the medical scanner 106, one or more settings of the medical scanner 106 are set. The patient 110 is imaged by the medical scanner 106 using the settings. In alternative embodiments, scan data from the medical scanner 106 is used to determine the surface data, such as by fitting a statistical shape model that includes a skin mesh to the scan data.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for internal body marker prediction from surface data in a medical imaging system, the method comprising:
   capturing, with a sensor, an outer surface of a patient, the surface data being from the capturing of the outer surface of the patient;
   generating, by an image processor, an image by a machine-learned network in response to input of the surface data to the machine-learned network, the image representing a location of the internal body marker of the patient; and
   displaying, by a display device, the image,
   wherein generating comprises generating with the machine-learned network having been trained with a joint loss function including an error and a penalty for centering and/or missing, and
   wherein the penalty comprises a loss regularizer, a landmark coefficient, a square root of a difference between argmax of the internal body marker and a ground truth of the internal body marker, and an absolute value of a difference between the maximum of the internal body marker and a ground truth of the internal body marker.

2. The method of claim 1 wherein capturing comprises capturing with the sensor being a depth sensor.

3. The method of claim 1 wherein capturing comprises capturing with the sensor being a camera where the surface data based on optical measurements.

4. The method of claim 1 wherein capturing further comprises fitting a statistical shape model to the output of the sensor for the outer surface, the surface data comprising (a) heights of the outer surface from a table and (b) thicknesses of the patient from the fit statistical shape model.

5. The method of claim 1 wherein capturing further comprises down sampling such that each pixel of the surface data is 1 cm or greater.

6. The method of claim 1 wherein generating comprises generating with the machine-learned network comprising a fully convolutional network with an encoder and a decoder.

7. The method of claim 6 wherein the encoder has fewer convolutional layers than the decoder and wherein the fully convolutional network has fewer than twelve convolutional layers.

8. The method of claim 1 wherein generating further comprises locating a plurality of other body markers and normalizing the surface data based on the other body markers, and wherein generating comprises generating the image with the internal body marker in response to input of the normalized surface data.

9. The method of claim 1 wherein the machine-learned network was trained with sequential iteration of the error and the joint loss function, the error comprising a mean square error.

10. The method of claim 9 wherein the sequential iteration starts using the mean square error as the loss function and ends where the mean square error is not decreasing.

11. The method of claim 1 wherein generating comprises generating the image to include the internal body marker and at least ten other body markers.

12. The method of claim 1 wherein displaying comprises displaying with the internal body marker labeled.

* * * * *